(12) United States Patent
Li

(10) Patent No.: US 11,994,506 B2
(45) Date of Patent: May 28, 2024

(54) MULTI-DIMENSIONAL DATA ACQUISITION AND ANALYSIS SYSTEM FOR PLACENTA TISSUE

(71) Applicant: East China Normal University, Shanghai (CN)

(72) Inventor: Qingli Li, Shanghai (CN)

(73) Assignee: EAST CHINA NORMAL UNIVERSITY, Shanghai (CN)

( * ) Notice: Subject to any disclaimer, the term of this patent is extended or adjusted under 35 U.S.C. 154(b) by 0 days.

(21) Appl. No.: 18/472,451

(22) Filed: Sep. 22, 2023

(65) Prior Publication Data

US 2024/0133862 A1 Apr. 25, 2024

(30) Foreign Application Priority Data

Oct. 20, 2022 (CN) .......................... 202211284350.6

(51) Int. Cl.
| | |
|---|---|
| *G01N 33/483* | (2006.01) |
| *A61B 5/107* | (2006.01) |
| *A61B 90/00* | (2016.01) |
| *G01N 33/48* | (2006.01) |

(Continued)

(52) U.S. Cl.
CPC ....... *G01N 33/4833* (2013.01); *A61B 5/1075* (2013.01); *A61B 5/1079* (2013.01); *A61B 90/00* (2016.02); *G01N 33/48* (2013.01); *G01N 33/483* (2013.01); *G06T 7/0012* (2013.01); *G06V 30/2247* (2022.01); *A61B 2562/0247* (2013.01);

(Continued)

(58) Field of Classification Search
CPC .. G01D 21/02; G01N 33/483; G01N 33/4833; G06T 2207/10036; G06T 2207/30024; A61B 5/1075; A61B 5/1079; A61B 2576/00
See application file for complete search history.

(56) References Cited

U.S. PATENT DOCUMENTS

2011/0160582 A1* 6/2011 Zheng ................ G01N 29/2481
367/87

FOREIGN PATENT DOCUMENTS

| CN | 102235980 | 11/2011 |
|---|---|---|
| CN | 210015057 | 2/2020 |
| CN | 111579563 | 8/2020 |

(Continued)

OTHER PUBLICATIONS

Notice of the First Office Action from SIPO in applicaiton No. 202211284350.6 dated Jun. 15, 2023.

(Continued)

*Primary Examiner* — William H Matthews
(74) *Attorney, Agent, or Firm* — Piloff Passino & Cosenza LLP; Rachel K. Piloff; Sean A. Passino

(57) ABSTRACT

A multi-dimensional data acquisition and analysis system for placenta tissue is provided, including a preparation area, a sampling area, a tension cable, a mobile platform, a tray, a mobile cabin door, a cabin door motor, a motor, a motor controller, binocular vision cameras, a laser point cloud detector, a hyperspectral camera, an ultrasonic ranging, a lifting motor, a lifting guide rail, ring light sources, an infrared sensor, a two-dimensional code area and a two-dimensional code identification camera. The technical scheme of the disclosure is adopted to solve the problem of lack of effective technical means for placenta detection at present.

6 Claims, 3 Drawing Sheets

(51) Int. Cl.
*G06T 7/00* (2017.01)
*G06V 30/224* (2022.01)

(52) U.S. Cl.
CPC ............... *G06T 2207/10036* (2013.01); *G06T 2207/30024* (2013.01)

(56) References Cited

FOREIGN PATENT DOCUMENTS

| CN | 212300868 | 1/2021 |
| CN | 114018384 | 2/2022 |

OTHER PUBLICATIONS

Retrieval report from SIPO in applicaiton No. 202211284350.6 dated Jun. 14, 2023.
Supplementary Retrieval report from SIPO in applicaiton No. 202211284350.6 dated Jun. 24, 2023.
Notification to Grant Patent Right for Invention from SIPO in applicaiton No. 202211284350.6 dated Jul. 31, 2023.

* cited by examiner

MULTI-DIMENSIONAL DATA ACQUISITION AND ANALYSIS SYSTEM FOR PLACENTA TISSUE

CROSS-REFERENCE TO RELATED APPLICATIONS

This disclosure claims priority to Chinese Patent Application No. 202211284350.6, filed on Oct. 20, 2022, the contents of which are hereby incorporated by reference.

TECHNICAL FIELD

The disclosure belongs to a technical field of placenta analysis, and in particular to a multi-dimensional data acquisition and analysis system for placenta tissue.

BACKGROUND

Placenta is a part of fetal appendages in the process of delivery, serving as an important organ for material exchange between a fetus and a mother, and the placenta is a tissue-binding organ between the mother and the fetus jointly grown by embryonic membrane and maternal endometrium during human pregnancy. Studies have shown that the placenta has certain reference significance for the diagnosing fetal and maternal diseases. At present, however, in the field of medicine, the placenta is mostly directly discarded, and only a few placentas are sent to the hospital pathology department for visual inspection and pathological examination. The main reason is that there is not enough attention paid to the placenta examination, and another reason is that there is still a lack of technical means for automatic placenta examination.

SUMMARY

The technical scheme of the disclosure is to provide a multi-dimensional data acquisition and analysis system for placenta tissue, so as to solve the problem of lack of effective technical means for placenta detecting at present.

In order to achieve the above objective, the disclosure adopts a following technical scheme:
a multi-dimensional data acquisition and analysis system for placenta tissue, including a preparation area, a sampling area, a tension cable, a mobile platform, a tray, a mobile cabin door, a cabin door motor, a motor, a motor controller, binocular vision cameras, a laser point cloud detector, a hyperspectral camera, an ultrasonic ranging, a lifting motor, a lifting guide rail, ring light sources, an infrared sensor, a two-dimensional code area and a two-dimensional code identification camera;

In the process of data acquisition, when the infrared sensor detects the placenta placed on the mobile platform, the mobile cabin door automatically opens under a control of the motor controller, and the motor drives the tension cable to pull the mobile platform into the sampling area. Then, the motor controller controls the cabin door motor to close the cabin door, turns on the ring light sources, starts the two-dimensional code identification camera to scan the two-dimensional code on the tray, starts the hyperspectral camera and the binocular vision cameras to collect data, and starts the laser point cloud detector and the ultrasonic ranging sensor to scan at a same time; after all data are acquired, the motor controller controls the cabin door motor to open the hatch, and the motor drives the tension cable to pull the mobile platform out of the sampling area and return to the preparation area; when samples are collected in the sampling area, the two-dimensional code identification camera scans the two-dimensional code area on the tray at the same time to obtain information of the collected placenta; the lifting motor drives the hyperspectral camera, the binocular vision cameras, the laser point cloud detector and the ultrasonic ranging sensor to move up and down along the lifting guide rail to meet measurement requirements of samples with different sizes.

Optionally, a housing is also included, and the lower half part of the housing is divided into the preparation area and the sampling area; the upper surface of the preparation area is provided with a preparation area guide rail, and the mobile platform is embedded into the preparation area guide rail through rollers; a first movable pulley is arranged at an outer corner of the preparation area, and the motor and the motor controller are arranged inside the preparation area; the upper surface of the mobile platform is provided with a groove, the tray is placed on the groove, and a tested placenta sample is placed on the tray; the upper surface of the mobile platform is provided with a standard color card and scale marks; the two-dimensional code area is on the upper surface of the tray; the sampling area is provided with the mobile cabin door near the preparation area guide rail, the infrared sensor is arranged on the mobile cabin door, and the mobile cabin door is connected with the housing of the sampling area through a cabin door slide rail; the upper end of the sampling area is provided with a touch screen and a level meter; the outer side surface of the sampling area is provided with a wiring channel; the lifting guide rail is arranged at the center of the top side inside the sampling area, the lifting motor is arranged on the lifting guide rail, camera connecting rods are fixedly arranged at both ends of the lifting motor, and the binocular vision cameras are arranged at both ends of the camera connecting rods, the hyperspectral camera is arranged at the lower sides of the middle positions of the camera connecting rods, and the laser point cloud detector and the ultrasonic ranging sensor are respectively arranged on the camera connecting rods at both sides of the hyperspectral camera; the ring light sources are installed in a circumferential direction at the inner side of the sampling area near a top position, a sampling area guide rail is arranged at the lower half part inside the sampling area parallel to the preparation area, a pressure sensor is arranged below the sampling area guide rail, and both ends of the pressure sensor are fixed at the inner side of the sampling area; a second movable pulley and a third movable pulley are installed at the inner side of the sampling area, and the tension cable is wound between the motor, the first movable pulley, the second movable pulley and the third movable pulley, and the two ends of the tension cable are respectively connected to the two ends of the mobile platform.

Optionally, the bottom surface inside the sampling area is provided with a wireless transmission module and a main control board; the bottom surface of the housing is provided with height-adjustable brackets; the wireless transmission module is in wireless connection with the smart phone and a trigger pedal; the control input end of the motor is connected to the output end of the motor controller, and the input end of the motor controller is connected to the control output end of the main control board; the data transmission end and the control end of the wireless transmission module are respectively connected to the data transmission end and the control end of the main control board; the signal output end of the infrared sensor is connected to the data input end of the main control board; the control input end of the cabin door motor is connected to the control output end of the main control board; the touch screen is connected with the main control board; the data output ends of the binocular vision cameras are connected to the data input end of the main control board; the data output end of the hyperspectral camera is connected to the data input end of the main control board; the output ends of the laser point cloud detector, the ultrasonic ranging sensor and the two-dimensional code identification camera are respectively connected to the input end of the main control board; the input ends of the ring light sources are connected to the output end of the main control board.

Optionally, the hyperspectral camera is one of a push-broom camera, a staring camera or a snapshot camera.

Optionally, bar codes are placed in the two-dimensional code area.

Optionally, the mobile platform is driven by the conveyor belt to move down into the sampling area or move out to the preparation area.

Optionally, the tray is a disposable transparent material tray.

Optionally, the wiring channel is arranged on the outer side of the sampling area.

In the disclosure, the placenta is taken as a detection target to carry out a multi-dimensional and multi-parameter data acquisition and analysis on the entire placenta; the analysis system of the disclosure adopts the binocular vision cameras to carry out a three-dimensional modeling on the placenta, adopts the hyperspectral camera to collect the placental tissue atlas data, adopts the laser scanning and the ultrasonic ranging to obtain accurate placental thickness information; and adopts the pressure sensor to obtain placental weight information. Based on multi-dimensional and multi-modal data of the placenta, the quantitative parameters of placenta size and umbilical cord length are automatically calculated by using image processing and analysis algorithm, thus providing a new equipment for the overall analysis and archiving of the placenta. The system may improve the automation and intelligence of placental examination, reduce the workload of manual interpretation and recording, and may also be used as an archive of placental data. In addition, the system may also be used to collect multi-dimensional and multi-modal data information of other surgically resected tissues. The device has a broad application prospect in delivery room and operating room.

BRIEF DESCRIPTION OF THE DRAWINGS

In order to explain the technical scheme of the present disclosure more clearly, the drawings needed in the embodiments are briefly introduced below. Obviously, the drawings described below are only some embodiments of the present disclosure, and other drawings may be obtained according to these drawings without creative work for ordinary technicians in the field.

DETAILED DESCRIPTION OF THE EMBODIMENTS

In the following, the technical scheme in the embodiments of the disclosure is clearly and completely described with reference to the attached drawings. Obviously, the described embodiments are only a part of the embodiments of the disclosure, but not the whole embodiments. Based on the embodiments in the present disclosure, all other embodiments obtained by ordinary technicians in the field without creative labor belong to the scope of protection of the present disclosure.

In order to make the above objects, features and advantages of the present disclosure more obvious and easier to understand, the present disclosure is further described in detail with the attached drawings and specific embodiments.

Embodiment 1

Figure 1:
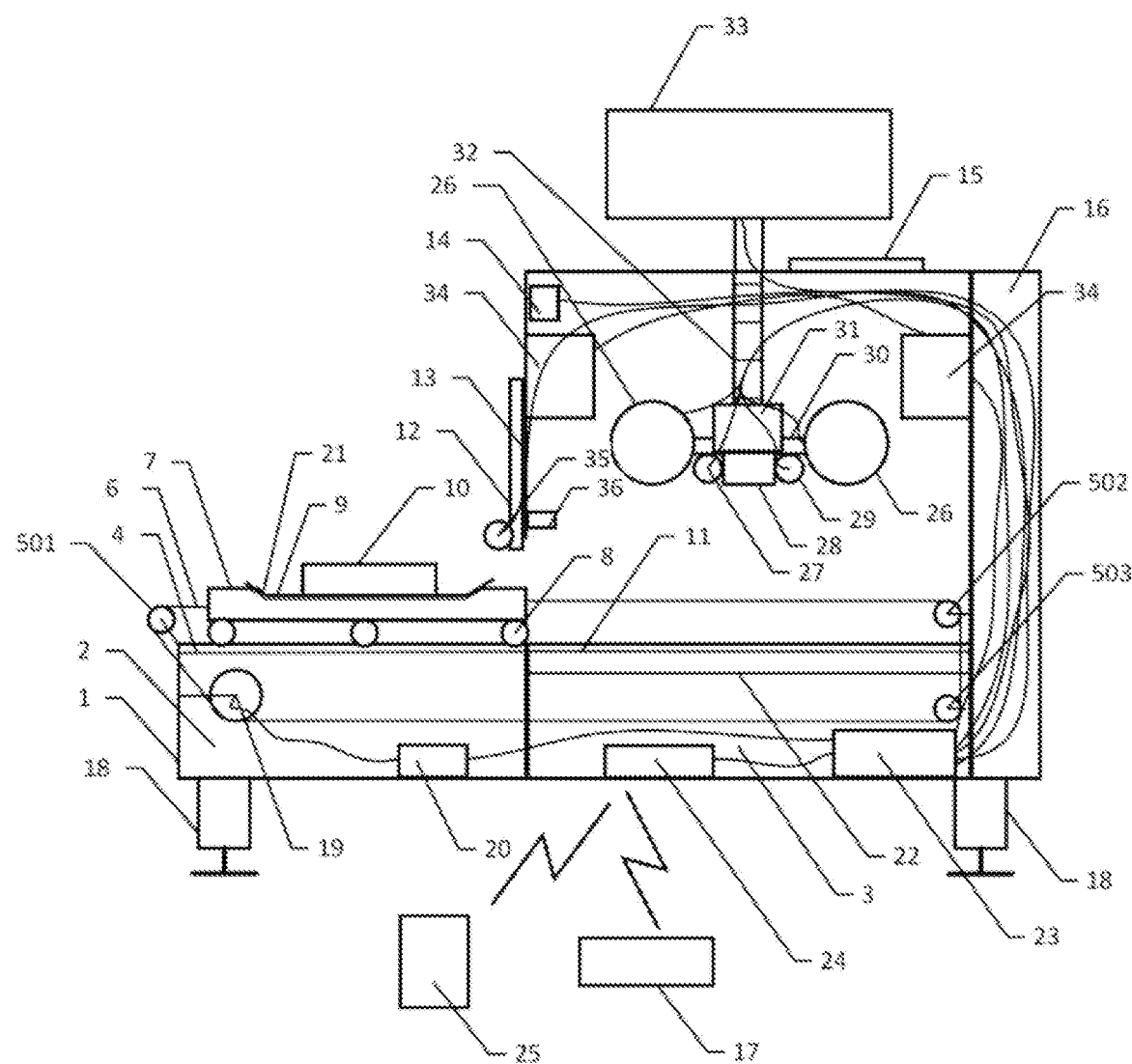
FIG. 1 is a schematic structural diagram of a multidimensional data acquisition and analysis system for placental tissue according to an embodiment of the present disclosure.
Figure 2:
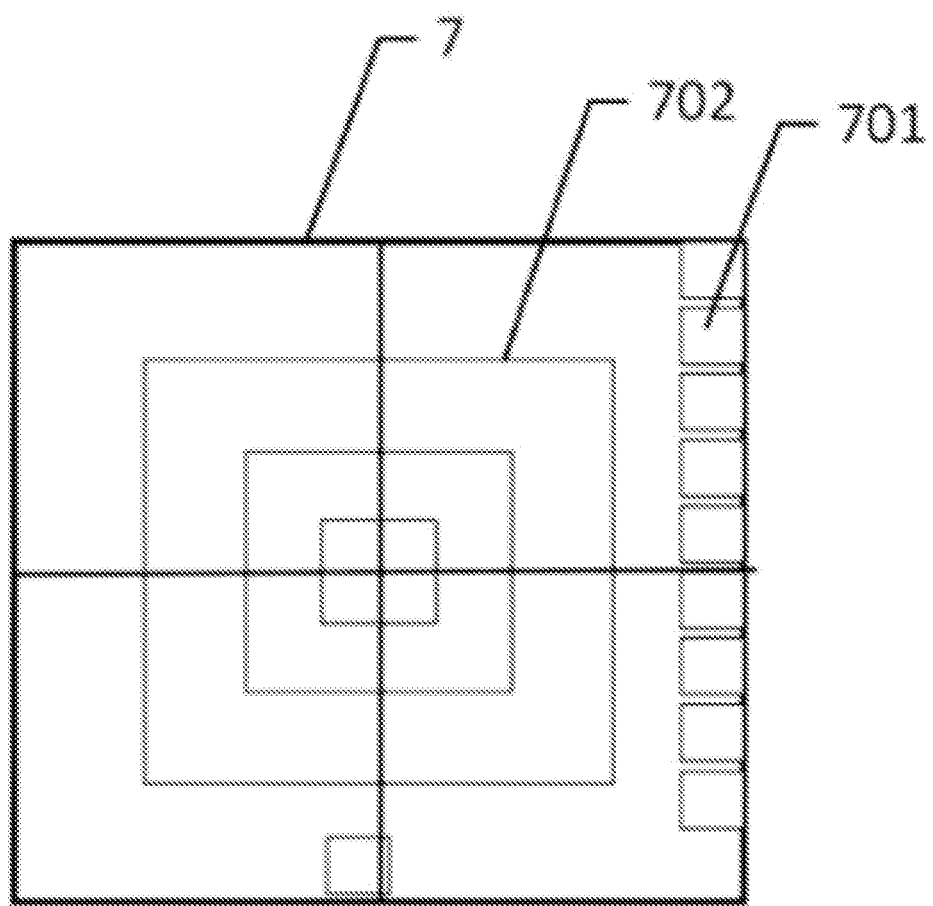
FIG. 2 is a schematic structural diagram of a mobile platform according to an embodiment of the present disclosure.
Figure 3:
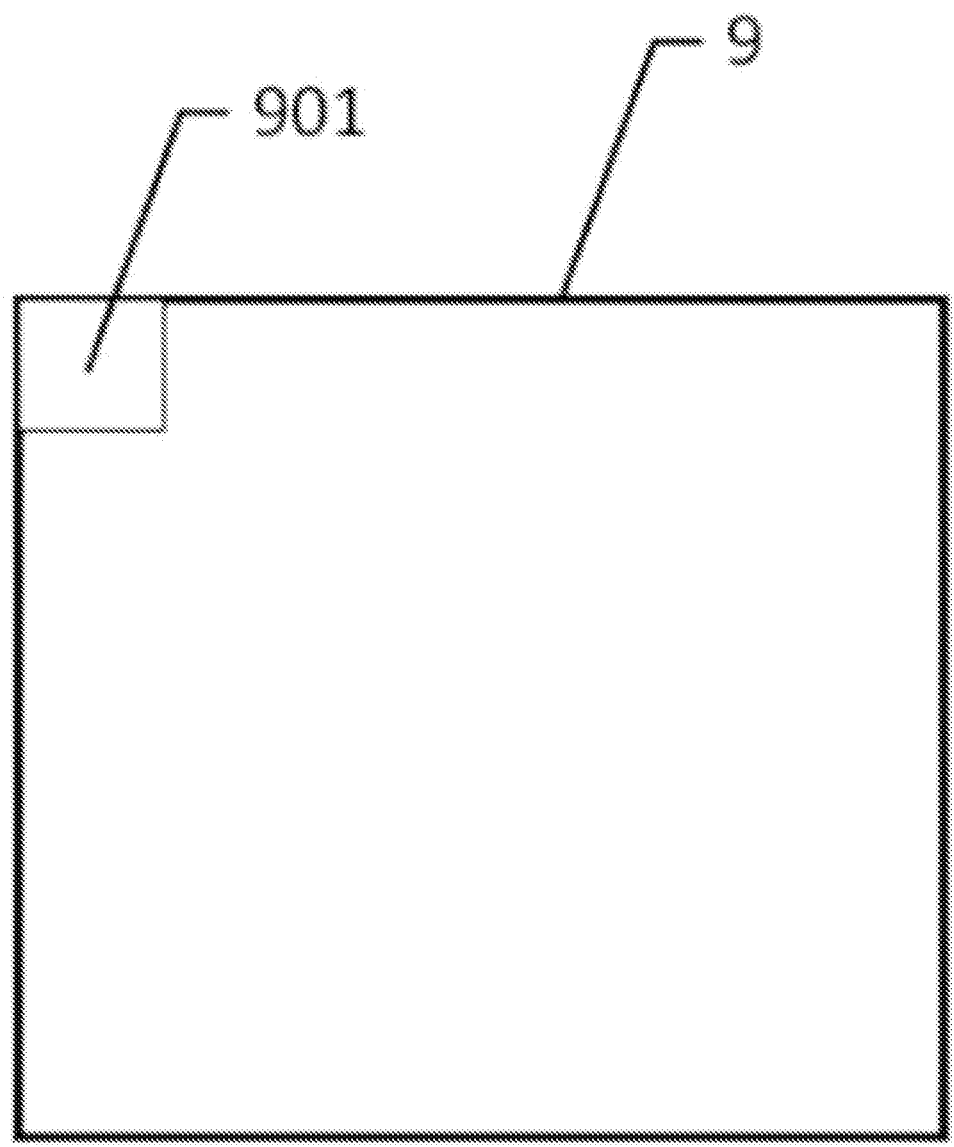
FIG. 3 is a schematic structural diagram of a tray according to an embodiment of the present disclosure.

As shown in FIG. 1, FIG. 2 and FIG. 3, a multi-dimensional data acquisition and analysis system for placenta tissue provided by the disclosure includes a housing 1, a preparation area 2, a sampling area 3, a preparation area guide rail 4, a first movable pulley 501, a second movable pulley 502, a third movable pulley 503, a tension cable 6, a moving platform 7, rollers 8, a tray 9, a placenta 10, a sampling area guide rail 11, a mobile cabin door 12, a cabin door slide rail 13, a cabin door motor 14, a gradienter 15, a wiring channel 16, a trigger pedal 17, height-adjustable brackets 18, a motor 19, a motor controller 20, a groove 21, a pressure sensor 22, a main control board 23, a wireless transmission module 24, a smart phone 25, binocular vision cameras 26, a laser point cloud 27, a hyperspectral camera 28, an ultrasonic ranging 29, camera connecting rods 30, a lifting motor 31, a lifting guide rail 32, a touch screen 33, ring light sources 34, an infrared sensor 35, a two-dimensional code area 901, a standard color card 701, a scale mark 702, and a two-dimensional code identification camera 36.

In this embodiment, the lower half part of the housing 1 is divided into the preparation area 2 and the sampling area 3. The upper surface of the preparation area 2 is provided with a preparation area guide rail 4, and the moving platform 7 is embedded into the preparation area guide rail 4 through rollers 8, a first movable pulley 501 is arranged at the outer corner of the preparation area 2, the motor 19 and the motor controller 20 are installed inside the preparation area 2, and the tension cable 6 is wound between the motor 19, the first movable pulley 501, the second movable pulley 502 and the third movable pulley 503, the two ends of the tension cable 6 are respectively connected with the two end of the mobile platform 7, the main control board 23 controls the rotation direction of the motor 19 through the motor controller 20, and under the tension of the tension cable 6, the mobile platform 7 translates into the sampling area 3 or moves into the preparation area 2 along the preparation area guide rail 4 and the sampling area guide rail 11. The upper surface of the mobile platform 7 is provided with a groove 21, the tray 9 is placed on the groove 21, the tested placenta sample 10 is placed on the tray 9, and the tray 9 is driven by the mobile platform 7 to move into or out of the sampling area; the upper surface of the mobile platform 7 is provided with the standard color card 701 for standardizing the colors of the collected images; the upper surface of the mobile platform 7 is also provided with the scale mark 702 for facilitating the photographing distance selection according to the size of the scaled sample; the two-dimensional code area 901 is on the upper surface of the tray 9, and the two-dimensional code of the placenta may be placed on the two-dimensional code area 901, and the two-dimensional code may be directly scanned during data acquisition to obtain sample information. The sampling area 3 is provided with the mobile cabin door 12 near the preparation area guide rail 4 of the preparation area 2, and the mobile cabin door 12 is provided with the infrared sensor 35, and the mobile cabin door 12 is connected with the housing 1 of the sampling area 3 through the cabin door slide rail 13, when the infrared sensor 35 detects the placenta 10 placed on the mobile platform 7, the mobile cabin door 12 automatically opens, and when the placenta 10 is completely moved into the sampling area 3, the mobile cabin door 12 is automatically closed; the touch screen 33 is installed at the upper end of the sampling area 3 to realize human-computer interaction and control the system; the gradienter 15 is installed at the upper end of the sampling area 3, and the system may be placed horizontally by adjusting the height-adjustable brackets 18 installed at the bottom of the housing 1; the outer side of the sampling area 3 is provided with a wiring channel 16 for facilitating the wiring of the system. The lifting guide rail 32 is installed at the center of the top side inside the sampling area 3, and the lifting motor 31 is installed on the lifting guide rail 32, the lifting motor 31 may drive the camera and other sensors on the lifting motor 31 to move up and down; the camera connecting rods 30 are fixed at both ends of the lifting motor 31, the binocular vision cameras 26 are installed at both ends of the camera connecting rods 30 for obtaining binocular information of the placenta 10 for three-dimensional reconstruction, and the hyperspectral camera 28 is arranged at the lower side of the middle position of the camera connecting rods 30 for collecting atlas data of the placenta; the camera connecting rods 30 on both sides of the hyperspectral camera 28 are respectively provided with the laser point cloud detector 27 for scanning the placenta morphology and the ultrasonic distance sensor 29 for measuring the thickness of a specific position of the placenta; the ring light sources 34 are installed around the top of the sampling area 3 for supplementary lighting on the sample; the sampling area guide rail 11 is arranged at the lower half part inside the sampling area 3 parallel to the preparation area 2, and a pressure sensor 22 is arranged below the sampling area guide rail 11, and both ends of the pressure sensor 22 are fixed at the inner side of the sampling area 3 for measuring the weight of the placenta 10; the wireless transmission module 24 is installed on the bottom surface inside the sampling area 3 for wireless connection with the smart phone 25 and the trigger pedal 17; the control input end of the motor 19 is connected to the output end of the motor controller 20, and the input end of the motor controller 20 is connected to the control output end of the main control board 23, so that the motor 19 may be controlled by the main control board 23 and the motor controller 20 to make the placenta move into or out of the sampling area 3; the main control board 23 may also control the opening and closing of the mobile cabin door 12, and may also obtain and store the measurement data of the binocular vision cameras 26, the laser point cloud detector 27, the hyperspectral camera 28 and the ultrasonic ranging sensor 29, read the data of the infrared sensor 35, and obtain the trigger switch information of the trigger pedal 17. The data of the pressure sensor 22 is used to measure the weight, control the work of the ring light sources 34, exchange information with the touch screen 33, and scan and identify the two-dimensional code on the tray 9 through the two-dimensional code identification camera 36.

As an implementation of this embodiment, the hyperspectral camera 28 may be a push-broom camera, a staring camera or a snapshot camera, and may also be a color camera or a gray scale camera.

As an implementation of this embodiment, bar codes are placed in the two-dimensional code area.

As an implementation of this embodiment, the mobile platform 7 is driven by the conveyor belt to move down into the sampling area 3 or move out to the preparation area 2.

As an implementation of this embodiment, the tray 9 is a disposable transparent material tray.

When collecting multidimensional data of the placenta 10, the placenta 10 to be test is first placed in the center of the tray 9, and the tray 9 is placed in the groove 21 of the mobile platform 7; after the infrared sensor 35 detects the placenta 10 sample on the tray 9, the infrared sensor 35 transmits the signal to the main control board 23, the main control board 23 controls the mobile cabin door 12 to open, and the control motor 19 drives the tension cable 6 to move the mobile platform 7 into the sampling area guide rail 11 of the sampling area 3; then, the main control board 23 controls the cabin door motor 14 to close the mobile cabin door 12, and collects the data of the pressure sensor 22 to obtain the weight data of the placenta 10. The main control board 23 turns on the ring light sources 34 for illumination, starts the two-dimensional code identification camera 36 to recognize the two-dimensional code of the two-dimensional code area 901 on the tray 9, and records the sample information of the placenta 10; when the user steps on the trigger pedal 17, the main control board 23 starts the hyperspectral camera 28 to collect the hyperspectral data of the placenta 10, starts the binocular vision cameras 26 to collect the stereoscopic vision data of the placenta 10, starts the laser point cloud detector 27 to perform a three-dimensional laser scanning on the placenta 10, and starts the ultrasonic distance sensor 29 to measure the thickness of the placenta. After data acquisition, the main control board 23 controls the motor 19 to drive the tension cable 6 to move the mobile platform 7 out of the sampling area 3, and the operator may take the tray 9 and replace with a new tray for the next use. According to the collected multidimensional image data of placenta 10 and the captured information of the standard color card 701, the main control board 23 calculated the color parameters of placenta 10 by comparison; further, the multi-dimensional and multi-modal data of the placenta 10 are comprehensively utilized to calculate the size of the placenta 10, the length of the umbilical cord and other data.

According to the disclosure, hyperspectral information, three-dimensional spatial image information and laser point cloud multidimensional image information of placenta postoperative tissue are synchronously obtained, that is, the weight and thickness data of placenta, three-dimensional spatial structure information and hyperspectral information are simultaneously obtained and quantitatively measured. According to the information obtained above, the placenta may be described quantitatively, including the maximum diameter, the minimum diameter, the placenta weight, the umbilical cord length, the umbilical cord insertion point and the placental color index. The disclosure provides data support for developing a new algorithm of artificial intelligence diagnosis of placental diseases, thus promoting the efficiency and objectivity of placental diagnosis and analysis.

The above-mentioned embodiments are only a description of the preferred mode of the disclosure, and do not limit the scope of the disclosure. Under the premise of not departing from the design spirit of the disclosure, various modifications and improvements made by ordinary technicians in the field to the technical scheme of the disclosure shall fall within the protection scope determined by the claims of the disclosure.

What is claimed is:

1. A multi-dimensional data acquisition and analysis system for placenta tissue, comprising a preparation area, a sampling area, a tension cable, a mobile platform, a tray, a mobile cabin door, a cabin door motor, a motor, a motor controller, binocular vision cameras, a laser point cloud detector, a hyperspectral camera, an ultrasonic ranging sensor, a lifting motor, a lifting guide rail, ring light sources, an infrared sensor, a two-dimensional code area and a two-dimensional code identification camera; wherein in a process of data acquisition, when the infrared sensor detects a placenta placed on the mobile platform, the mobile cabin door automatically opens under a control of the motor controller, and the motor drives the tension cable to pull the mobile platform into the sampling area, then the motor controller controls the cabin door motor to close the cabin door, turns on the ring light sources, starts the two-dimensional code identification camera to scan a two-dimensional code on the tray, starts the hyperspectral camera and the binocular vision cameras to collect data, and starts the laser point cloud detector and the ultrasonic ranging sensor to scan at a same time; after all data are acquired, the motor controller controls the cabin door motor to open the cabin door, and the motor drives the tension cable to pull the mobile platform out of the sampling area and return to the preparation area; when samples are collected in the sampling area, the two-dimensional code identification camera scans the two-dimensional code area on the tray at a same time to obtain information of the collected placenta; the lifting motor drives the hyperspectral camera, the binocular vision cameras, the laser point cloud detector and the ultrasonic ranging sensor to move up and down along the lifting guide rail to meet measurement requirements of samples with different sizes;

the system also comprises a housing, and a lower half part of the housing is divided into the preparation area and the sampling area; an upper surface of the preparation area is provided with a preparation area guide rail, and the mobile platform is embedded into the preparation area guide rail through rollers; a first movable pulley is arranged at an outer corner of the preparation area, and the motor and the motor controller are arranged inside the preparation area; an upper surface of the mobile platform is provided with a groove, the tray is placed on the groove, and a tested placenta sample is placed on the tray; the upper surface of the mobile platform is provided with a standard color card and scale marks; the two-dimensional code area is on an upper surface of the tray; the sampling area is provided with the mobile cabin door near the preparation area guide rail, the infrared sensor is arranged on the mobile cabin door, and the mobile cabin door is connected with the housing of the sampling area through a cabin door slide rail; an upper end of the sampling area is provided with a touch screen and a level meter; an outer side surface of the sampling area is provided with a wiring channel; the lifting guide rail is arranged at a center of a top side inside the sampling area, the lifting motor is arranged on the lifting guide rail, a first set of camera connecting rods is fixedly arranged at a first end of the lifting motor and a second set of camera connecting rods is fixedly arranged at a second end of the lifting motor, and the binocular vision cameras are arranged at both ends of each respective set of the camera connecting rods, the hyperspectral camera is arranged at a lower side of a middle position of the camera connecting rods, and the laser point cloud detector is fixedly attached to the first set of camera connecting rods and is arranged on one side of the hyperspectral camera and the ultrasonic ranging sensor is fixedly attached to the second set of camera connecting rods and is arranged on the other side of the hyperspectral camera; the ring light sources are installed in a circumferential direction at an inner side of the sampling area near a top position, a sampling area guide rail is arranged at a lower half part inside the sampling area parallel to the preparation area, a pressure sensor is arranged below the sampling area guide rail, and the pressure sensor is fixed at both ends within the inner side of the sampling area; a second movable pulley and a third movable pulley are installed at the inner side of the sampling area, and the tension cable is wound between the motor, the first movable pulley, the second movable pulley and the third movable pulley, and the tension cable is respectively connected to the two ends of the mobile platform.

2. The multi-dimensional data acquisition and analysis system for placenta tissue according to claim 1, wherein a bottom surface inside the sampling area is provided with a wireless transmission module and a main control board; a bottom surface of the housing is provided with height-adjustable brackets; the wireless transmission module is in wireless connection with a smart phone and a trigger pedal; a control input end of the motor is connected to an output end of the motor controller, and the output end of the motor controller is connected to a control output end of the main control board; a data transmission end and a control end of the wireless transmission module are respectively connected to a data transmission end and a control end of the main control board; a signal output end of the infrared sensor is connected to a data input end of the main control board; a control input end of the cabin door motor is connected to the control output end of the main control board; the touch screen is connected with the main control board; data output ends of the binocular vision cameras are connected to the data input end of the main control board; a data output end of the hyperspectral camera is connected to the data input end of the main control board; output ends of the laser point cloud detector, the ultrasonic ranging sensor and the two-dimensional code identification camera are respectively connected to the input end of the main control board; input ends of the ring light sources are connected to the output end of the main control board.

3. The multi-dimensional data acquisition and analysis system for placenta tissue according to claim 2, wherein the hyperspectral camera is one of a push-broom camera, a staring camera or a snapshot camera.

4. The multi-dimensional data acquisition and analysis system for placenta tissue according to claim 3, wherein bar codes are placed in the two-dimensional code area.

5. The multi-dimensional data acquisition and analysis system for placenta tissue according to claim 3, wherein the mobile platform is driven by a conveyor belt to move down into the sampling area or move out to the preparation area.

6. The multi-dimensional data acquisition and analysis system for placenta tissue according to claim 5, wherein the tray is a disposable transparent material tray.

* * * * *